US012662529B2

(12) United States Patent
Pippig et al.

(10) Patent No.: US 12,662,529 B2
(45) Date of Patent: *Jun. 23, 2026

(54) PRODUCTION OF BIOSIMILAR USTEKINUMAB IN CHO CELLS

(71) Applicant: FYB202 Project GmbH, Martinsried/Planegg (DE)

(72) Inventors: Susanne Pippig, Munich (DE); Carsten Brockmeyer, Marzling (DE)

(73) Assignee: FYB202 PROJECT GMBH, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 19/048,808

(22) Filed: Feb. 7, 2025

(65) Prior Publication Data

US 2025/0230231 A1 Jul. 17, 2025

Related U.S. Application Data

(63) Continuation of application No. 17/572,350, filed on Jan. 10, 2022, now abandoned, which is a continuation of application No. 16/322,846, filed as application No. PCT/EP2017/069522 on Aug. 2, 2017, now abandoned.

(30) Foreign Application Priority Data

Aug. 3, 2016 (EP) .................................... 16182661

(51) Int. Cl.

| | |
|---|---|
| ***A61K 39/395*** | (2006.01) |
| ***A61K 9/00*** | (2006.01) |
| ***A61K 47/18*** | (2017.01) |
| ***A61K 47/20*** | (2006.01) |
| ***A61K 47/22*** | (2006.01) |
| ***A61K 47/26*** | (2006.01) |
| ***C07K 16/24*** | (2006.01) |
| *A61K 39/00* | (2006.01) |

(52) U.S. Cl.

CPC .......... *C07K 16/244* (2013.01); *A61K 9/0019* (2013.01); *A61K 47/183* (2013.01); *A61K 47/20* (2013.01); *A61K 47/22* (2013.01); *A61K 47/26* (2013.01); *A61K 2039/54* (2013.01); *C07K 2317/14* (2013.01); *C07K 2317/21* (2013.01); *C07K 2317/41* (2013.01); *C07K 2317/76* (2013.01); *C07K 2317/92* (2013.01)

(58) Field of Classification Search

None

See application file for complete search history.

(56) References Cited

U.S. PATENT DOCUMENTS

| | | | | |
|---|---|---|---|---|
| 8,962,804 B2 * | 2/2015 | Williams | A61K 47/6877 530/300 | |
| 12,098,196 B2 | 9/2024 | Pippig et al. | | |
| 2005/0009097 A1 * | 1/2005 | Better | A61P 35/00 435/7.1 | |
| 2013/0126742 A1 | 5/2013 | Hayun et al. | | |
| 2013/0216742 A1 * | 8/2013 | DeMartino | C03C 3/091 428/34.4 | |
| 2020/0347126 A1 | 11/2020 | Pippig et al. | | |
| 2022/0204607 A1 | 6/2022 | Pippig et al. | | |

FOREIGN PATENT DOCUMENTS

| | | | |
|---|---|---|---|
| EP | 3059319 A1 | 8/2016 | |
| EP | 3493843 A1 | 6/2019 | |
| WO | WO-2002012500 A2 | 2/2002 | |
| WO | WO-2012012271 A2 * | 1/2012 | C07K 16/4283 |
| WO | WO-2012149197 A2 | 11/2012 | |
| WO | WO-2015053523 A1 | 4/2015 | |

OTHER PUBLICATIONS

Bort, J.A., et al., "CHO-K1 host cells adapted to growth in glutamine-free medium by FACS-assisted evolution," Biotechnology Journal 5:1090-1097, Wiley-VCH Verlag GMBH, Germany (2010).

Chung, C.H., et al., "Cetuximab-Induced Anaphylaxis and IgE Specific for Galactose-α-1,3-Galactose," N Eng J. Med 358(11):1109-1117, Massachusetts Medical Society, United States (2008).

Diaz, S.L., et al., "Sensitive and Specific Detection of the Non-Human Sialic Acid N-Glycolylneuraminic Acid In Human Tissues and Biotherapeutic Products," PLoS One 4(1):e4241, Public Library of Science, United States (2009).

Dumont, J., et al., "Human cell lines for biopharmaceutical manufacturing: history, status, and future perspectives," Crit. Rev. Biotechnol. 36(6): 1110-1122, Taylor & Francis, United States (2015).

Gramer, M.J., et al., "Modulation of Antibody Galactosylation Through Feeding of Uridine, Manganese Chloride, and Galactose," Biotechnol. Bioeng. 108(7): 1591-1602, Wiley Online Library, United States (2011).

Kaneko, Y., et al., "Anti-Inflammatory Activity of Immunoglobulin G Resulting from Fc Sialylation," Sciencemag.org 313:670-673, American Association for the Advancement of Science, United States (2006).

Kao, T-F., et al., "Genetics Of Somatic Mammalian Cells, Vii. Induction And Isolation Of Nutritional Mutants In Chinese Hamster Cells," Genetics: 1275-1281, Genetics Society of America, United States (1968).

Kaufman, R.J., et al., "Overview of Vector Design for Mammalian Gene Expression," Molecular Biotechnology 16(2):151-160, Springerlink, United States (2000).

Makrides, S.C., "Components of Vectors for gene Transfer and Expression in Mammalian Cells," Protein Expression and Purification 17:183-202, Academic Press, United States (1999).

(Continued)

*Primary Examiner* — Yunsoo Kim

(74) *Attorney, Agent, or Firm* — Sterne, Kessler, Goldstein & Fox P.L.L.C.

(57) ABSTRACT

The present invention relates to a method for producing an ustekinumab antibody in CHO cells. It further relates to the use of the produced antibody in the treatment of plaque psoriasis, psoriatic arthritis and inflammatory bowel disease.

26 Claims, No Drawings

Specification includes a Sequence Listing.

(56) References Cited

OTHER PUBLICATIONS

Onitsuka, M., et al., "Enhancement of sialylation on humanized IgG-like bispecific antibody by overexpression of α2,6-sialyltransferase derived from Chinese hamster ovary cells," Appl Microbiol Biotechnol 94:69-80, Springer, Germany (2012).
Padler-Karavani, et al., "Diversity in specificity, abundance, and composition of anti-Neu5Gc antibodies in normal humans: potential implications for disease," Glycobiology 18(10):818-830, Oxford Journals, England (2008).
Raju, T.S., et al., "Galactosylation variations in marketed therapeutic antibodies," mABS 4(3):385-391, Landes Biosciences, United States (2012).
Rohrer, J.S., et al., "Analysis of the N-acetylneuraminic acid and N-glycolylneuraminic acid contents of glycoproteins by high-pH anion-exchange chromatography with pulsed amperometric detection (HPAEC/PAD)," Glycobiology 8(1):35-43, Oxford University Press, United Kingdom (1998).
Ruhaak, L.R., et al., "Glycan labeling strategies and their use in identification and quantification," Anal Bioanl Chem 397:3457-3481, Springerlink, United States (2010).
Scallon, B.J., et al., "Higher Levels of sialylated Fc glycans in immunoglobulin G molecules can adversely impact functionality," Molecular Immunology 44:1524-1534, Elsevier (2007).
Tijo, J.H., et al., "Genetics of Somatic Mammalian Cells: II Chromosomal Constitution of Cells in Tissue Culture," J Exp Med 108(2): 259-268, Rockefeller University Press, United States (1958).
Yu, C., et al., "At least two Fc Neu5Gc residues of monoclonal antibodies are required for binding to anti-Neu5Gc antibody," Scientific Reports 6:20029, Nature Publishing, England (2016).
Benson, J.M., et al., "Discovery and mechanism of ustekinumab: a human monoclonal antibody targeting interleukin-12 and interleukin-23 for treatment of immune-mediated disorders," *MAbs* 3(6):535-545, Landes Bioscience, United States (Aug. 2011).
Dhara, V.G., et al., "Recombinant Antibody Production in CHO and NS0 Cells: Differences and Similarities," *BioDrugs* 32:571-584, Adis International Ltd., United Kingdom (Nov. 2018).
Walsh, G., "Biopharmaceutical benchmarks 2018," Nat Biotechnology 36(12):1136-1145, Nature Publishing Group, United Kingdom (2018).
European Medicines Agency, Stelara, INN-ustekinumab, Annex I, Summary of Product Characteristics, 182 pages.
Formycon AG, "Formycon's Biosimilar U stekinumab Candidate Fyb202 Shows Comparable Efficacy to Reference Product Stelara®* in Phase III Study," accessed at https://www.formycon.com/en/blog/press-release/formycons-biosimilar-ustekinumab-candidate-fyb202-shows-comparable-efficacy-to-reference-product-stelara-in-phase-iii-study/ (Aug. 2022).
Borys, M.C., et al., "Effects of culture conditions on N-glycolylneuraminic acid (Neu5Gc) content of a recombinant fusion protein produced in CHO cells," Biotechnol Bioeng 105(6):1048-1057, Wiley, United States (Apr. 2010).
International Search Report and Written Opinion for International Application No. PCT/EP2017/069522, European Patent Office, Netherlands, mailed on Oct. 26, 2017, 17 pages.
Janssen, "ustekinumab New Zealand Data Sheet," www.medsafe.govt.nz, accessed at https://www.medsafe.govt.nz/profs/datasheet/s/stelarainj.pdf, accessed on Feb. 3, 2025, 44 pages.
Read, E.K., et al., "Industry and regulatory experience of the glycosylation of monoclonal antibodies," Biotechnol Appl Biochem. 58(4):213-219, Wiley, United States (Jul.-Aug. 2011).
Sandborn, W.J., et al. "Ustekinumab induction and maintenance therapy in refractory Crohn's disease," N Engl J Med. 367(16):1519-1528, Massachusetts Medical Society, United States (Oct. 2012).
Schwaigerlehner, L., "Antibody gene expression in CHO cells with recombinase mediated cassette exchange," University of Natural Resources and Life Sciences Vienna, Austria (Nov. 2015), 105 pages.
Xu, X., et al., "The genomic sequence of the Chinese hamster ovary (CHO)-K1 cell line," Nat Biotechnol. 29(8):735-741, Springer Nature, Germany (Jul. 2011).
Zhang, L., et al., "Recombinase-mediated cassette exchange (RMCE) for monoclonal antibody expression in the commercially relevant CHOK1SV cell line," Biotechnol Prog. 31(6):1645-1656, Wiley, United States (Oct. 2015).

* cited by examiner

SEQUENCE LISTING

```
Sequence total quantity: 2
SEQ ID NO: 1          moltype = AA  length = 449
FEATURE               Location/Qualifiers
source                1..449
                      mol_type = protein
                      note = heavy chain of ustekinumab
                      organism = synthetic construct
SEQUENCE: 1
EVQLVQSGAE VKKPGESLKI SCKGSGYSFT TYWLGWVRQM PGKGLDWIGI MSPVDSDIRY  60
SPSFQGQVTM SVDKSITTAY LQWNSLKASD TAMYYCARRR PGQGYFDFWG QGTLVTVSSS  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449
```

-continued

```
SEQ ID NO: 2            moltype = AA  length = 214
FEATURE                 Location/Qualifiers
source                  1..214
                        mol_type = protein
                        note = light chain of ustekinumab
                        organism = synthetic construct
SEQUENCE: 2
DIQMTQSPSS LSASVGDRVT ITCRASQGIS SWLAWYQQKP EKAPKSLIYA ASSLQSGVPS  60
RFSGSGSGTD FTLTISSLQP EDFATYYCQQ YNIYPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214
```

PRODUCTION OF BIOSIMILAR USTEKINUMAB IN CHO CELLS

FIELD OF THE INVENTION

The present invention relates to a method for producing an ustekinumab antibody in CHO cells. It further relates to the use of the produced antibody in the treatment of plaque psoriasis, psoriatic arthritis and inflammatory bowel disease.

BACKGROUND OF THE INVENTION

Ustekinumab which is marketed under the name Stelara® is a fully human IgG1κ antibody which binds to the common p40 subunit of the cytokines IL-12 and IL-23. The antibody-bound cytokines can no longer bind to their cognate receptors and are therefore not able to elicit an inflammatory response in a patient's body. In Europe ustekinumab has received a marketing authorization for the treatment of moderate to severe plaque psoriasis and active psoriatic arthritis as well as for the treatment of moderately to severely active Crohn's disease.

Stelara® (ustekinumab) is expressed in a Sp2/0 murine myeloma cell line using a protein-free, chemically defined cell culture medium and purified by a series of affinity and ion exchange chromatographic steps and viral inactivation steps.

A biosimilar therapeutic antibody is a therapeutic antibody which is marketed after patent and data protection for the original product (also referred to as reference product) has expired and which has the same amino acid sequence as the original product, but may slightly differ in posttranslational modifications due to the use of another production process. Nevertheless, the biosimilar therapeutic antibody has to show a similar safety and efficacy profile as the reference product. In terms of safety the content of N-glycolylneuraminic acid (NGNA) and α1,3-galactose are important parameters, since these elements are potentially immunogenic and can cause hypersensitivity reactions (Chung et al. (2008) N. Engl. J. Med. 358: 1109-1117; Padler-Karavani et al. (2008) Glycobiology 18: 818-830). With respect to efficacy the binding of the antibody to its target and the Fc-mediated activity are important parameters. Further, the binding of the antibody to FcRn may influence the pharmacokinetic behaviour of the antibody.

The mouse Sp2/0 cells used in the production of the ustekinumab reference product produce a lower titer of the recombinant protein than the CHO cells. On the other hand, mouse cells are known to produce highly sialylated proteins and it is known that a human anti-IL12/IL23 antibody produced in SP2/0 cells has a high sialic acid content (Raju and Jordan (2012) mAbs 4:3, 385-391; Yu et al. (2016) Scientific Reports 7: 20029). According to the scientific literature the sialic acid content influences the target binding and the Fc mediated activity of antibodies (Scallon et al. (2007) Mol. Immunol. 44: 1524-1534; Kaneko et al. (2006) Science 313: 670-673).

WO 2012/012271 A1 and Dumont et al. (2016) Crit. Rev. Biotechnol. 36(6): 1110-1122 disclose that ustekinumab is produced in CHO cells. The Master thesis of Linda Schwaigerlehner ("Antibody gene expression in CHO cells with recombinase mediated cassette exchange") submitted in November 2015 and EP 3 059 319 A1 describe the production of ustekinumab in CHO cells, but do not provide any analysis of the produced antibody with respect to sialylation and activity.

Nevertheless, it was believed that a biosimilar ustekinumab has to be produced in the Sp2/0 cells to exert the same functions as the reference ustekinumab product.

SUMMARY OF THE INVENTION

The present inventors have surprisingly found that an ustekinumab antibody produced in CHO cells having a low sialic acid content shows essentially the same biological activity as the ustekinumab reference antibody.

Accordingly, the present invention relates to a method of producing a recombinant ustekinumab antibody drug product comprising the heavy chain and the light chain of ustekinumab, wherein the heavy chain has the sequence according to SEQ ID No. 1 and the light chain has the sequence according to SEQ ID No. 2 and wherein the heavy chain and the light chain together form the recombinant ustekinumab antibody, the method comprising:

a) culturing Chinese Hamster Ovary (CHO) host cells, genetically engineered to express the heavy chain and the light chain of ustekinumab, in a suitable culture medium under conditions that allow the cells to express the heavy chain and the light chain and to form the recombinant ustekinumab antibody;
b) harvesting the recombinant ustekinumab antibody from the host cell culture to obtain a recombinant ustekinumab antibody preparation;
c) optionally purifying the recombinant ustekinumab antibody preparation obtained in step b) by one or more purification step(s);
d) determining that the recombinant ustekinumab antibody in the recombinant ustekinumab antibody preparation obtained in step b) or c) meets one or more of the following criteria (i) to (iv):
   (i) binding to IL-23 differs from that of the reference product by not more than 10%;
   (ii) binding to IL-12 differs from that of the reference product by not more than 20%;
   (iii) binding to FcRn differs from that of the reference product by less than 10%; and
   (iv) inhibition of IL12- and/or IL23-induced target gene expression differs from that of the reference product by not more than 20%; and
e) combining the recombinant ustekinumab antibody from the recombinant ustekinumab antibody preparation with one or more pharmaceutically acceptable excipients to obtain the recombinant ustekinumab antibody drug product.

Preferably, the IL12 and/or IL23 target gene is interferon gamma.

The binding to IL-23, IL-12 and/or FcRn or the expression of the target gene may be determined by ELISA or bio-layer interferometry.

Preferably, in step d) it is determined that the recombinant ustekinumab antibody in the recombinant ustekinumab antibody preparation meets all criteria (i) to (iv).

In one embodiment in step d) it is further determined that the recombinant ustekinumab antibody in the recombinant ustekinumab antibody preparation meets one or more of the following criteria (v) to (viii):

(v) sialic acid content≤5%,
(vi) >90% of the sialic acid being N-acetylneuraminic acid,
(vii) <10% of the sialic acid being N-glycolylneuraminic acid, and
(viii) <50% of the recombinant ustekinumab antibody molecules comprise a C-terminal lysine.

In one embodiment in step d) it is further determined that the recombinant ustekinumab antibody in the recombinant ustekinumab antibody preparation meets one or more of the following criteria (ix) to (xi):

(ix) content of galactosylated glycoforms of at least 30%;

(x) content of afucosylated glycoforms of less than 8%; and (xi) content of high mannose glycoforms of less than 3%.

The CHO host cells may be CHO-K1 cells or cells derived therefrom.

The CHO host cells may be cultured in fed-batch mode.

The recombinant ustekinumab antibody drug product may be produced in large scale.

In one embodiment the one or more pharmaceutically acceptable excipient(s) is/are selected from the group consisting of sucrose, L-histidine, L-histidine monohydrochloride monohydrate and polysorbate 80.

Preferably, the recombinant ustekinumab antibody drug product comprises 90 mg/mL recombinant ustekinumab antibody, 1 mg/mL L-histidine/L-histidine monohydrochloride monohydrate, 0.04 mg/mL polysorbate 80, 76 mg/mL sucrose and water for injection.

The recombinant ustekinumab antibody drug product produced according to the method described herein may be used in treating plaque psoriasis or psoriatic arthritis.

In one embodiment the one or more pharmaceutically acceptable excipient(s) is/are selected from the group consisting of sucrose, L-histidine, L-histidine monohydrochloride monohydrate, EDTA disodium salt dihydrate, methionine and polysorbate 80.

Preferably, the recombinant ustekinumab antibody drug product comprises 5 mg/mL recombinant ustekinumab antibody, 1.8 mg/mL L-histidine/L-histidine monohydrochloride monohydrate, 0.4 mg/mL polysorbate 80, 85 mg/mL sucrose, 0.02 mg/ml EDTA disodium salt dehydrate, 0.4 mg/ml methionine and water for injection.

The recombinant ustekinumab antibody drug product produced according to the method described herein may be used in treating Crohn's disease.

DETAILED DESCRIPTION OF THE INVENTION

The present invention as illustratively described in the following may suitably be practiced in the absence of any element or elements, limitation or limitations, not specifically disclosed herein.

The present invention will be described with respect to particular embodiments, but the invention is not limited thereto, but only by the claims.

Where the term "comprising" is used in the present description and claims, it does not exclude other elements. For the purposes of the present invention, the term "consisting of" is considered to be a preferred embodiment of the term "comprising". If hereinafter a group is defined to comprise at least a certain number of embodiments, this is also to be understood to disclose a group which preferably consists only of these embodiments.

Where an indefinite or definite article is used when referring to a singular noun, e.g. "a", "an" or "the", this includes a plural of that noun unless something else is specifically stated.

Within the meaning of the present invention the term "composition" is to be understood in its broadest sense and refers to any composition in which the ustekinumab antibody is stable for at least some hours. Accordingly, the term composition includes cell culture media into which the ustekinumab antibody has been secreted, buffered salt solutions which result from one or more purification steps and pharmaceutical compositions which are intended to be administered to a patient. The composition typically comprises a mixture of several ustekinumab antibody molecules wherein the single antibody molecules may differ from each other in their glycosylation and charge due to a different degree of sialylation and the presence or absence of C-terminal lysine residues.

The term "antibody preparation" refers to a composition comprising the ustekinumab antibody which has been harvested from the host cell culture or to a composition which has been purified by one or more chromatographic steps. It does not refer to a composition which comprises the antibody and one or more pharmaceutically acceptable excipients.

The term "antibody drug product" refers to a composition which is ready to be administered to a patient for treating a disease. Accordingly, the antibody drug product comprises the antibody and one or more pharmaceutically acceptable excipients. As used herein, the term "antibody drug product" is equivalent to the term "pharmaceutical composition".

Ustekinumab which is marketed under the name Stelara® is a fully human IgG1κ antibody which binds to the p40 subunit of both IL-12 and IL-23 and thereby blocks the inflammatory response in a patient's body. The amino acid sequences of the heavy and light chain of ustekinumab are displayed in SEQ ID Nos. 1 and 2 herein. In Europe ustekinumab has received a marketing authorization for the treatment of moderate to severe plaque psoriasis and of active psoriatic arthritis as well as for the treatment of moderately to severely active Crohn's disease.

The ustekinumab antibody is glycosylated on the asparagine residue 299 of the Fc region of the antibody. The glycan attached to the Fc region via said asparagine residue has the following general formula:

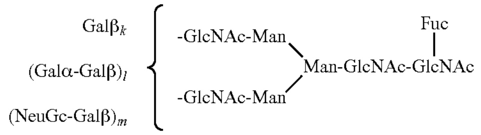

k, l, m = 0, 1, 2; k + l + m = 0, 1, 2 wherein GlcNAc refers to N-acetylglucosamine, Fuc refers to fucose, Galβ refers to a galactose residue which is β1,4-linked to an N-acetylglucosamine residue, Galα refers to a galactose residue which is α1,3-linked to galactose, NeuGc refers to sialic acid and Man refers to mannose.

The glycoform wherein k, l and m in the above formula are each 0 is called the G0F glycoform. In addition, the antibody may be in the afucosylated form lacking the fucose attached to the N-acetylglucosamine. In this case the glycoform is denoted as G0.

To one or both terminal N-acetylglucosamine residues a galactose residue may be attached so that in this case k in the above formula is 1 or 2. The glycoform with one galactose residue (k=1 in the above formula) is called G1F (or G1 in case the fucose is not present) and the glycoform with two galactose residues (k=2 in the above formula) is called G2F (or G2 in case the fucose is not present).

Further, sialic acid residues may be attached to one or both galactose residues of the G1F/G1 or G2F/G2 structures so that in this case m in the above formula is 1 or 2 and l is 0 or 1. Instead of the one or two sialic acid residues one or two α-galactose residues may be linked to the terminal galactose, resulting in a terminal Gal-α1,3-Gal linkage (l in the above formula is 1 or 2 and m is 0).

As discussed above, the ustekinumab antibody which is produced by the method of the present invention has a low sialic acid content. In particular, the sialic acid content of the ustekinumab antibody which is produced by the method of the present invention is significantly lower than the sialic acid content of the ustekinumab antibody produced in mouse cells, such as Sp2/0 cells.

Additionally, a glycoform may be present in which additional mannose residues are added to the mannose residues in the structure above so that the glycoform has the following structure:

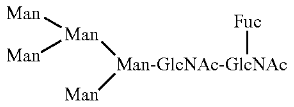

wherein GlcNAc refers to N-acetylglucosamine, Fuc refers to fucose and Man refers to mannose. This glycoform is also called Man5 or M5.

Within the meaning of the present invention the term "reference product" is used to denote the product with which the biosimilar product is compared to show similarity and bioequivalence. The reference product is therefore the product which has already obtained marketing approval. In the case of ustekinumab, the reference product is the approved Stelara® product or the ustekinumab antibody as present in the approved Stelara® product, respectively. For determining the similarity in the glycosylation between the reference product and the biosimilar, the ustekinumab antibody as present in the approved Stelara® product is used. The ustekinumab antibody is described in WO 2002/012500 A2.

"Sialic acid" is used to denote a group of compounds which are derivatives of the nine-carbon sugar neuraminic acid. The most common sialic acid forms in recombinant proteins are N-acetylneuraminic acid (NANA) and N-glycolylneuraminic acid (NGNA).

The term "sialic acid content" refers to the percentage of sialylated N-glycans in relation to the total amount of N-glycans in the glycoproteins within the composition. These glycoproteins are typically a mixture of glycoproteins with different glycan structures such as the G1F glycoform with one sialic acid molecule attached and the G2F glycoform with one or two sialic acid molecules attached.

The sialic acid content of the ustekinumab antibody which is produced by the method of the present invention is between 0 and 9%, preferably between 0.1 and 7% or between 0.1 and 5%, more preferably between 0.1 and 4% or between 0.1 and 3% or between 0.2 and 2.5%, even more preferably between 0.2 and 2% or between 0.2 and 1.8% and most preferably it is between 0.2 and 1.5% or between 0.2 and 1.4%.

For determining the sialic acid content the N-linked glycans are first released from the antibody by enzymatic reaction using a glycosidase such as PNGase F or PNGase A and then separated from the protein. Afterwards, the N-linked glycans are labelled with a suitable label including, but not being limited to, 2-AB (2-aminobenzamide), 2-AA (2-aminobenzoic acid), PA (2-aminopyridine), ANTS (2-aminonaphthalene trisulfonic acid), APTS (1-aminopyrene-3,6,8-trisulfonic acid) and RapiFluor-MS™ reagent. Suitable labelling kits are commercially available, for example the GlycoProfile™ 2-AB Labeling Kit of Sigma Aldrich, the Signal™ 2-AB Labeling Kit of ProZyme and the GlycoWorks RapiFluor-MS N-Glycan kit of Waters. Preferably, 2-AB or RapiFluor-MS™ reagent are used for labelling. The identification of glycans by labelling and subsequent detection is described in detail in Ruhaak et al. (2010) Anal. Bioanal. Chem. 397: 3457-3481.

After purification of the labelled N-linked glycans from the excess reagent they are separated and detected by a suitable method such as hydrophilic interaction liquid chromatography (HILIC), gel permeation chromatography or gas chromatography. Preferably, HILIC is used for separating and detecting N-linked glycans. Suitable stationary phases comprise amine-bonded silica, amide-bonded silica, ZIC HILIC phases and diol phases. Suitable columns are commercially available, such as the Xbridge Glycan BEH Amide XP Column (130 Å, 2.5 μm, 2.1 mm×150 mm) of Waters. Suitable mobile phases comprise water in acetonitrile with a low concentration of acid or salt. Preferably, 50-100 mM ammonium formate in acetonitrile is used.

The sample comprising the N-linked glycans may be applied to the column in 50% acetonitrile and may be eluted from the column by increasing the percentage of ammonium formate in the solution. The peaks corresponding to the specific N-glycans, in particular the sialylated N-glycans, can be identified by comparison to the peaks of a standard or by mass spectrometry. The mass spectrometry also allows to distinguish between NGNA- and NANA-sialylated glycans. The sialic acid content is calculated as the percentage of the area of the peaks of all sialylated glycoforms in relation to the area of the peaks of all glycoforms within the sample.

The sialic acid present in the ustekinumab antibody of the present invention is predominantly N-acetylneuraminic acid (NANA), i.e. at least 90% or 91%, preferably at least 92% or 93%, more preferably at least 94% or 95%, even more preferably at least 96% or 97% and most preferably at least 98% or 99% of all sialic acids attached to the ustekinumab antibody produced by the method of the present invention are NANA.

The NANA content can also be determined using commercially available kits (e.g. Sialic Acid (NANA) Assay Kit ab83375 of abcam; Sialic Acid Quantitation Kit of Sigma-Aldrich) which measure the NANA content after its release from glycoproteins by enzymatic digestion using neuraminidase or acid hydrolysis. The released NANA can then be detected for example by an enzyme-coupled reaction in which free sialic acid is oxidized to an intermediate which then reacts with a probe to a product which can be detected by absorbance or fluorescence. Alternatively, the released NANA can be labeled with the fluorescent agent DMB (4,5-methylene-dioxy-1,2-phenylenediamine dihydrochloride) and detected by RP-HPLC. As described above, the NANA content can also be determined by mass spectrometry.

The ustekinumab antibody which is produced by the method of the present invention contains only low amounts of N-glycolylneuraminic acid (NGNA), i.e. less than 10% or 9%, preferably less than 8% or 7%, more preferably less than 6% or 5%, even more preferably less than 4% or 3% and most preferably less than 2% or 1% of all sialic acids attached to the ustekinumab antibody produced by the method of the present invention are NGNA. NGNA can be detected and quantified using NGNA-specific antibodies (see, e.g., Diaz et al. (2009) PloS ONE 4(1): e4241). As described above, the NGNA content can also be determined by mass spectrometry.

The content of NANA and NGNA can also be determined using high-performance anion-exchange chromatography with pulsed amperometric detection (HPAEC-PAD) which additionally allows to distinguish between NANA and NGNA (Rohrer et al. (1998) Glycobiol. 8(1): 35-43). The sialic acid species which is attached to sialylated N-glycans can also be determined using liquid chromatography, a mass detector and the GlycoWorks RapiFluor-MS N-Glycan kit of Waters.

In the ustekinumab antibody which is produced by the method of the present invention at least 90% or 91% of all sialic acids attached to the ustekinumab antibody produced by the method of the present invention are NANA and less than 10% or 9% of all sialic acids attached to the ustekinumab antibody produced by the method of the present invention are NGNA, preferably at least 92% or 93% of all sialic acids attached to the ustekinumab antibody produced by the method of the present invention are NANA and less than 8% or 7% of all sialic acids attached to the ustekinumab antibody produced by the method of the present invention are NGNA, more preferably at least 94% or 95% of all sialic acids attached to the ustekinumab antibody produced by the method of the present invention are NANA and less than 6% or 5% of all sialic acids attached to the ustekinumab antibody produced by the method of the present invention are NGNA, even more preferably at least 96% or 97% of all sialic acids attached to the ustekinumab antibody produced by the method of the present invention are NANA and less than 4% or 3% of all sialic acids attached to the ustekinumab antibody produced by the method of the present invention are NGNA and most preferably at least 98% or 99% of all sialic acids attached to the ustekinumab antibody produced by the method of the present invention are NANA and less than 2% or 1% of all sialic acids attached to the ustekinumab antibody produced by the method of the present invention are NGNA.

The inventors have further observed that the ustekinumab antibody produced by the method of the present invention has a lower amount of terminal α-galactose, which is linked to the terminal galactose of the G1/G1F or G2/G2F glycoforms by an α1,3-linkage, than in the reference product. Thus, the content of terminal α-galactose as defined above is less than or equal to 0.1%. The content of terminal α-galactose can be determined as described above for the sialic acid content.

The composition produced by the method of the present invention also differs from the reference product marketed as Stelara® in the distribution of the G0F and G2F glycoforms. The content of the G0F glycoform is at least 35%, preferably at least 40% or 42%, more preferably at least 45% or 48% and most preferably at least 50%. The content of the G0F glycoform is between 35% and 70%, preferably between 40% or 42% and 70%, more preferably between 45% or 48% and 68% and most preferably between 50% and 68% or between 55% and 65%. The content of the G2F glycoform is less than 6.5%, preferably less than 6.2%, more preferably less than 6% and most preferably less than 5.8%. The content of the G2F glycoform is between 1.5% and 6.5%, preferably between 1.8% or 2% and 6.2%, more preferably between 2.2% and 6% and most preferably between 2.4% and 5.8%.

The content of the G0F glycoform is at least 35% and the content of the G2F glycoform is less than 6.5%. Preferably, the content of the G0F glycoform is at least 40% or 42% and the content of the G2F glycoform is less than 6.2%. More preferably, the content of the G0F glycoform is at least 45% or 48% and the content of the G2F glycoform is less than 6%. Most preferably, the content of the G0F glycoform is at least 50% and the content of the G2F glycoform is less than 5.8%. The content of the G0F glycoform is between 35% and 70% and the content of the G2F glycoform is between 1.5% and 6.5%. Preferably, the content of the G0F glycoform is between 40% or 42% and 70% and the content of the G2F glycoform is between 1.8% or 2% and 6.2%. More preferably, the content of the G0F glycoform is between 45% or 48% and 68% and the content of the G2F glycoform is between 2.2% and 6%. Most preferably, the content of the G0F glycoform is between 50% and 68% or between 55% and 65% and the content of the G2F glycoform is between 2.4% and 5.8%.

The content of the G0F and G2F glycoforms can be determined as described above for the sialic acid content.

The ustekinumab antibody produced by the method of the present invention has a content of galactosylated glycoforms of at least 30%, preferably of at least 32%, more preferably of at least 34% and most preferably of at least 35%. The ustekinumab antibody produced by the method of the present invention has a content of galactosylated glycoforms of between 25% and 50%, preferably of between 30% and 45%, more preferably of between 32% and 42% and most preferably of between 33% and 40%. The content of galactosylated glycoforms can be determined by calculating the sum of the percentages of glycoforms having at least one galactose residue, i.e. glycoforms G1F, G1, G2 and G2F.

The ustekinumab antibody produced by the method of the present invention has a content of afucosylated glycoforms of less than 8%, preferably less than 7%, more preferably less than 6% and most preferably of less than 5%. The ustekinumab antibody produced by the method of the present invention has a content of afucosylated glycoforms of between 0.5% to 8%, preferably between 0.8% and 7%, more preferably between 1% and 6% and most preferably between 1.5% and 4%. The content of afucosylated glycoforms can be determined by calculating the sum of the percentages of glycoforms which do not comprise at least one fucose.

The ustekinumab antibody produced by the method of the present invention has a content of high mannose (M5) glycoforms of less than 3%, preferably of less than 2.5%, more preferably less than 2.2% and most preferably of less than 1.8%. The ustekinumab antibody produced by the method of the present invention has a content of high mannose (M5) glycoforms of between 0.1% and 3%, preferably between 0.2% and 2.5%, more preferably between 0.3% and 2.2% and most preferably between 0.4% and 1.8%. The content of the high mannose glycoform can be determined as described above for the sialic acid content.

Another difference between the ustekinumab antibody produced by the method of the present invention and the antibody present in the reference product marketed as Stelara® as well as an antibody produced in Sp2/0 cells is the percentage of antibody molecules having a C-terminal lysine residue. The term "C-terminal lysine residue" refers to the lysine residue which is located on the C-terminus of the IgG1 heavy chain constant region and therefore terminates the CH3 domain of the heavy chain constant region.

At least 50% of the ustekinumab molecules produced by the method of the present invention do not comprise a C-terminal lysine residue. Preferably at least 53% or 56%, more preferably at least 58% or 60% and most preferably at least 63% of the ustekinumab molecules produced by the method of the present invention do not comprise a C-terminal lysine residue. Further, from 50 to 75% of the ustekinumab molecules do not comprise a C-terminal lysine residue. Preferably, 52% to 74% or 55% to 73%, more preferably 57% to 72% or 60% to 71% and most preferably 63% to 70% of the ustekinumab molecules produced by the method of the present invention do not comprise a C-terminal lysine residue. These numbers refer to the main peak of the protein having no C-terminal lysine residue as obtained by cation exchange chromatography.

The percentage of antibody molecules which comprise no, one or two C-terminal lysine residues can be determined by any suitable method including cation exchange chromatography (CEX), isoelectric focusing (IEF), capillary zone electrophoresis (CZE), capillary isoelectric focusing (cIEF) and liquid chromatography-mass spectrometry (LC-MS), preferably it is determined using cation exchange chromatography. For example, a sample of the antibody may be loaded onto a weak cation exchange chromatography column having carboxyl groups as functional groups in a solution containing 20 mM sodium phosphate buffer, pH 7.5 and the antibody may be eluted by sequentially increasing the percentage of a salt-containing buffer such as 20 mM sodium phosphate buffer, pH 7.5 and 25 mM NaCl. The peaks corresponding to proteins with no, one or two C-terminal lysine residues can be identified by treatment with specific enzymes or mass spectrometry. The percentage of antibody molecules which do not comprise a C-terminal lysine residue can be calculated as the ratio of the peak area for the isoform having no lysine residue to the total peak area. The above percentage is calculated using the main peak representing the protein with no C-terminal lysine residue as obtained by cation exchange chromatography performed as described above and in the examples section.

As discussed before, the present inventors have surprisingly found that despite the lower sialic acid content the ustekinumab antibody which is produced by the method of the present invention essentially has the same biological activity as the reference product Stelara® and an ustekinumab antibody produced in mouse cells. The biological activity of the ustekinumab antibody includes one or more of binding to IL-23, binding to IL-12, binding to FcRn and inhibition of IL12-induced gene expression.

The binding of the antibody to IL-23, IL-12 or FcRn may be assessed using methods including, but not being limited to, ELISA and bio-layer interferometry.

The skilled person is aware of protocols for performing an ELISA assay. In brief, the target of the antibody, i.e. IL-12 or IL-23 in case of ustekinumab, is coated onto a plate, incubated with the ustekinumab antibody, washed and then the bound antibody is detected and quantified with a labelled antibody specific for human IgG.

Bio-layer interferometry is a label-free optical analytical technique which analyzes the interference pattern of white light reflected from two surfaces, i.e. a layer of immobilized protein on the biosensor tip and an internal reference layer. The binding of molecules to the biosensor tip, e.g. by interaction of an antibody with its cognate target, leads to a shift in the interference pattern that can be measured in real-time. For measuring the interaction between ustekinumab and its target the ustekinumab antibody is immobilized on the biosensor tip and contacted with a solution containing the target protein.

The binding of the ustekinumab antibody produced by the method of the present invention to IL-12 or IL-23 is essentially the same as that of the reference product, i.e. the binding to IL-12 or IL-23 differs by less than 20%, preferably by less than 15% from the binding of the reference product.

Surprisingly, it has been found that the binding of the ustekinumab antibody produced by the method of the present invention to IL-23 and IL-12 is similar to the binding of the reference product to IL-23 and IL-12.

The binding of the ustekinumab antibody produced by the method of the present invention to IL-23 differs by not more than 10%, preferably by not more than 9%, more preferably by not more than 8%, even more preferably by not more than 7% and most preferably by not more than 5% from the binding of the reference product to IL-23.

The binding of the ustekinumab antibody produced by the method of the present invention to IL-12 differs by not more than 20%, preferably by not more than 15%, more preferably by not more than 12% and most preferably by not more than 10% from the binding of the reference product to IL-12.

The binding of the ustekinumab antibody produced by the method of the present invention to FcRn is essentially the same as that of the reference product, i.e. the dissociation constant $K_D$ for binding to FcRn differs by less than 10%, preferably by less than 8%, more preferably by less than 6% and most preferably by less than 4% from the dissociation constant $K_D$ of the reference product.

The inhibition of IL12-induced gene expression by the ustekinumab antibody can for example be investigated by incubating cells which are responsive to IL-12, such as the human natural killer lymphoma cell line NK-92, with IL-12 and the antibody sample and then detecting the production of a target molecule, such as interferon-gamma (IFN-γ). The target molecule, e.g. IFNγ, may be detected and/or quantified by any suitable method, such as ELISA.

Surprisingly, it has been found that the inhibition of IFNγ production by the ustekinumab antibody produced by the method of the present invention is as strong as the inhibition of IFNγ production by the reference product. The inhibition of IFNγ production by the ustekinumab antibody produced by the method of the present invention differs by not more than 16%, preferably by not more than 14%, more preferably by not more than 12% and most preferably by not more from 10% from the inhibition of IFNγ production by the reference product.

The method of the present invention comprises determining that the recombinant ustekinumab antibody preparation meets one or more of the following criteria (i) to (iv):

(i) binding to IL-23 differs from that of the reference product by not more than 10%;
(ii) binding to IL-12 differs from that of the reference product by not more than 20%;
(iii) binding to FcRn differs from that of the reference product by less than 10%; and
(iv) inhibition of IL12- and/or IL23-induced target gene expression differs from that of the reference product by not more than 20%.

Preferably, the target gene of IL12 and/or IL23 is interferon gamma.

In one embodiment, the method of the present invention comprises determining that the recombinant ustekinumab antibody preparation meets one of the above criteria (i) to (iv). In one embodiment, the method of the present invention comprises determining that the recombinant ustekinumab antibody preparation meets two of the above criteria (i) to (iv), such as criteria (i) and (ii), (i) and (iii), (i) and (iv), (ii) and (iii), (ii) and (iv) or (iii) and (iv). In one embodiment, the method of the present invention comprises determining that the recombinant ustekinumab antibody preparation meets three of the above criteria (i) to (iv), such as criteria (i), (ii) and (iii) or (ii), (iii) and (iv). In one embodiment, the method of the present invention comprises determining that the recombinant ustekinumab antibody preparation meets all four of the above criteria (i) to (iv).

The determination whether the recombinant ustekinumab antibody preparation meets above criterion (i) comprises measuring the binding of the recombinant ustekinumab antibody preparation and the reference product to IL-23 and calculating the difference in binding. The determination whether the recombinant ustekinumab antibody preparation meets above criterion (ii) comprises measuring the binding of the recombinant ustekinumab antibody preparation and the reference product to IL-12 and calculating the difference in binding. The determination whether the recombinant ustekinumab antibody preparation meets above criterion (iii) comprises measuring the binding of the recombinant ustekinumab antibody preparation and the reference product to FcRn and calculating the percentage of different binding. The determination whether the recombinant ustekinumab antibody preparation meets above criterion (iv) comprises measuring the expression of a known target gene of IL12 and/or IL23 in cells treated with the recombinant ustekinumab antibody preparation or the reference product and calculating the difference in target gene expression. If the target gene is interferon gamma, the interferon gamma production in cells treated with the recombinant ustekinumab antibody preparation or the reference product is measured and the difference in interferon gamma production is calculated.

The method of the present invention may additionally comprise determining that the recombinant ustekinumab antibody preparation meets one or more of the following criteria (v) to (viii):

(v) sialic acid content≤5%, (vi) >90% of the sialic acid being N-acetylneuraminic acid, (vii) <10% of the sialic acid being N-glycolylneuraminic acid, and (viii) <50% of the recombinant ustekinumab antibody molecules comprise a C-terminal lysine.

In one embodiment, the method of the present invention comprises determining that the recombinant ustekinumab antibody preparation meets one of the above criteria (v) to (viii). In one embodiment, the method of the present invention comprises determining that the recombinant ustekinumab antibody preparation meets two of the above criteria (v) to (viii), such as criteria (v) and (vi), (v) and (vii), (v) and (viii), (vi) and (vii), (vi) and (viii) or (vii) and (viii). In one embodiment, the method of the present invention comprises determining that the recombinant ustekinumab antibody preparation meets three of the above criteria (vi) to (viii), such as criteria (v), (vi) and (vii) or (vi), (vii) and (viii). In one embodiment, the method of the present invention comprises determining that the recombinant ustekinumab antibody preparation meets all four of the above criteria (v) to (viii).

The method of the present invention may additionally comprise determining that the recombinant ustekinumab antibody preparation meets one or more of the following criteria (ix) to (xi):

(ix) content of galactosylated glycoforms of at least 30%;

(x) content of afucosylated glycoforms of less than 8%; and (xi) content of high mannose glycoforms of less than 3%.

In one embodiment, the method of the present invention comprises determining that the recombinant ustekinumab antibody preparation meets one of the above criteria (ix) to (xi). In one embodiment, the method of the present invention comprises determining that the recombinant ustekinumab antibody preparation meets two of the above criteria (ix) to (xi), such as criteria (ix) and (x), (ix) and (xi) or (x) and (xi). In one embodiment, the method of the present invention comprises determining that the recombinant ustekinumab antibody preparation meets all three of the above criteria (ix) to (xi).

As discussed above, according to the present invention the ustekinumab antibody is produced in CHO cells. CHO cells are epithelial cells which are derived from the ovary of the Chinese hamster ovary (Tijo and Puck (1958) J. Exp. Med. 108: 259-271). From the original CHO cell line several other cell lines have been obtained, including CHO-K1, CHO-Toronto, CHO-DXB11, CHO-DG44 and CHO K1 SV. All these cell lines can be used to produce the composition comprising ustekinumab according to the present invention.

Preferably, a CHO-K1 cell line or cells derived therefrom is used to produce the composition comprising ustekinumab of the present invention. The CHO-K1 cell line has been obtained from a single clone of the original CHO cells (Kao and Puck (1968) Proc. Nat. Acad. Sci. USA 60(4): 1275-1281). The CHO-K1 cell line can be adapted to suspension growth and/or to a chemically defined medium (see, e.g., Bort et al. (2010) Biotechnol. J. 5(10): 1090-1097). In the present invention preferably CHO-K1 cells or cells derived therefrom are used. The cells which are derived from the CHO-K1 cells are cells which originate from the CHO-K1 cells, but have been subjected to one or more adaptation processes, such as adaptation to serum-free medium or suspension growth.

The CHO cells used to produce the ustekinumab antibody have been genetically modified to express the ustekinumab antibody. The term "genetically modified CHO cells" as used herein means that CHO cells have been modified or altered by any suitable genetic means and methods known to the skilled person such that they express the ustekinumab antibody. In one embodiment, the genetic modification to express the ustekinumab antibody is the only genetic modification of the CHO cells. In another embodiment the CHO cells are genetically modified to increase or decrease the expression of one or more enzymes which have an impact on the sialic acid content of proteins, such as sialyltransferases or sialidases. In one embodiment, the CHO cells are genetically modified to decrease the expression of one or more sialidases. In another embodiment the CHO cells are genetically modified to increase the expression of one or more sialyltransferases. A CHO cell line which is genetically modified to express an α2,6-sialyltransferase is described in Onitsuka et al. (2012) Appl. Microbiol. Biotechnol. 94: 69-80. Preferably, the CHO cells do not comprise a genetic modification other than the genetic modification to express the ustekinumab antibody.

Methods for genetically modifying CHO cells are known to the skilled person and particularly include the transfection of the CHO cells with one expression vector encoding the heavy and the light chain of the antibody or with a first expression vector encoding the heavy chain of the antibody and a second expression vector encoding the light chain of the antibody. In one embodiment, the recombinant antibody is produced from one recombinant nucleic acid molecule which encodes both the heavy and the light chain of the antibody. In a more preferred embodiment, the recombinant antibody is produced from two recombinant nucleic acid molecules having the same or different promoters. In an even more preferred embodiment, the recombinant antibody is produced from two recombinant nucleic acid molecules having the same promoter. In a most preferred embodiment, the recombinant antibody is produced from two recombinant nucleic acid molecules which differ from each other only by the encoded gene and the selection marker used to select the transfected cells.

The elements and methods needed to construct expression vectors which are suitable for expressing an antibody in CHO cells are well-known to the skilled person and described for example in Makrides et al. (1999) Protein Expr. Purif. 17: 183-202 and Kaufman (2000) Mol. Biotechnol. 16: 151-161. Further, the skilled person is aware of methods for introducing the expression vectors into the CHO cells. These methods include the use of commercially available transfection kits such as Lipofectamine® of ThermoFisher, PEImax of Polyplus Sciences) or Freestyle Max of Invitrogen. Further suitable methods include electroporation, calcium phosphate-mediated transfection and DEAE-dextrane transfection. After transfection the cells are subjected to selection by treatment with a suitable agent based on the selection marker(s) encoded by the expression vector(s) to identify the stably transfected cells.

To produce the ustekinumab antibody the genetically modified CHO cells are cultured in a suitable culture medium. The terms "medium", "cell culture medium" and "culture medium" are interchangeably used herein and refer to a solution containing nutrients which are required for growing mammalian cells. Typically, a cell culture medium provides essential and non-essential amino acids, vitamins, energy sources, lipids, and trace elements required by the cell for minimal growth and/or survival. Preferably, the medium is chemically defined in that all its components and their concentration are known. Also preferably, the medium is serum-free and hydrolysate-free and does not contain any components derived from animals. More preferably, the medium is chemically defined, serum-free, animal-component-free and hydrolysate-free.

Media for growing CHO cells are commercially available and include PowerCHO-2 CD available from Lonza, CD OptiCHO™ Medium available from ThermoFisher and EX-CELL® CD CHO Serum-Free Medium available from Sigma-Aldrich. These media may be supplemented with further reagents such as recombinant insulin, lipids, ferric citrate, PEG20000, extra amounts of some sugar types and extra amounts of some or all amino acids.

Preferably, the CHO cells are cultured in suspension, i.e. in a non-adherent state.

The galactose content of the antibody may be increased by adding suitable amounts of galactose, manganese ions and/or uridine to the cell culture medium (Gramer et al. (2011) Biotechnol. Bioeng. 108(7): 1591-1602; WO 2012/149197 A2).

For culturing the CHO cells different strategies are available, including batch culture, continuous culture and fed-batch culture. Within the present invention, preferably a fed-batch culture process is used to produce ustekinumab. In fed-batch culture the culturing process is started with a certain volume of the medium and one or more nutrients are fed at later time-point(s) of the culture process to prevent nutrient depletion while no product is removed from the cell culture broth.

The method of the present invention may be used to produce ustekinumab in large scale, i.e. in a production volume of at least 50 l or 100 l, preferably of at least 500 l or at least 1.000 l, more preferably of at least 5.000 l and most preferably of at least 10.000 l or 20.000 l.

After the ustekinumab antibody has been produced by the CHO cells, it is harvested. Since recombinant proteins, in particular antibodies, expressed from mammalian cells are typically secreted into the cell culture fluid during the cultivation process, the product harvest at the end of the cultivation process occurs by separating cell culture fluid comprising the ustekinumab antibody from the cells. The cell separation method should be gentle to minimize cell disruption to avoid the increase of cell debris and release of proteases and other molecules that could affect the quality of the immunoglobulin product. Usually, the harvesting of the cell culture fluid comprising the ustekinumab involves centrifugation and/or filtration, whereby the recombinant protein is present in the supernatant and the filtrate, respectively. Expanded bed adsorption chromatography is an alternative method to avoid centrifugation/filtration methods.

After harvesting the cell culture fluid comprising the ustekinumab antibody, the antibody has to be purified from the cell culture fluid. The purification of recombinant proteins and in particular recombinant antibodies is usually accomplished by a series of chromatographic steps such as anion exchange chromatography, cation exchange chromatography, affinity chromatography, hydrophobic interaction chromatography, hydroxyapatite chromatography, mixed mode chromatography and size exclusion chromatography. The purification of recombinant antibodies usually starts with a protein A affinity chromatography to capture the antibody and is followed by one or more additional chromatographic steps such as cation exchange chromatography and mixed mode chromatography. Further, the purification process may comprise one or more ultra-, nano- or diafiltration steps.

Also described herein is a pharmaceutical composition comprising an ustekinumab antibody, wherein the antibody has a sialic acid content of 0 to 5%.

A pharmaceutical composition is a composition which is intended to be delivered to a patient for treating or preventing a disease or condition. In addition to the active agent, in the present case the ustekinumab antibody, a pharmaceutical composition also contains at least one pharmaceutically acceptable excipient. Pharmaceutically acceptable excipients are substances which do not interfere with the physiological activity of the active agent such as the ustekinumab antibody and which stabilize the pharmaceutical composition and/or enhance solubility or decrease viscosity of the pharmaceutical composition. Typical pharmaceutically acceptable excipients for monoclonal antibodies include buffers, salts, sugars or sugar alcohols, amino acids and surface-active agents.

The pharmaceutical composition preferably contains sucrose, L-histidine, L-histidine monohydrochloride monohydrate and polysorbate 80. More preferably, the pharmaceutical composition of the present invention contains 76 mg/mL sucrose, 1 mg/mL L-histidine/L-histidine monohydrochloride monohydrate and 0.04 mg/mL polysorbate 80 in water for injection (WFI). Most preferably, the pharmaceutical composition consists of 90 mg/mL ustekinumab antibody as characterized herein, 76 mg/mL sucrose, 1 mg/mL L-histidine, 1 mg/mL L-histidine monohydrochloride monohydrate and 0.04 mg/mL polysorbate 80 in water for injection (WFI).

The pharmaceutical composition described above can be used in the treatment of plaque psoriasis, in particular the treatment of moderate to severe plaque psoriasis in adults who failed to respond to, or who have a contraindication to, or are intolerant to other systemic therapies including cyclosporin, methotrexate (MTX) or PUVA (psoralen and ultraviolet A) and the treatment of moderate to severe plaque psoriasis in adolescent patients from the age of 12 years and older, who are inadequately controlled by, or are intolerant to, other systemic therapies or phototherapies and psoriatic arthritis, in particular the treatment of active psoriatic arthritis in adult patients when the response to previous non-biological disease-modifying anti-rheumatic drug (DMARD) therapy has been inadequate.

The pharmaceutical composition may also be used in the treatment of adult patients with moderate to severe plaque psoriasis (Ps) who are candidates for phototherapy or systemic therapy or for the treatment of active psoriatic arthritis (PsA), alone or in combination with methotrexate.

The recommended dosage of ustekinumab for the treatment of adult patients having plaque psoriasis or psoriatic arthritis is 45 mg or 90 mg, depending on the body weight, administered subcutaneously, followed by a 45 mg or 90 mg dose 4 weeks later, and then every 12 weeks thereafter.

In another embodiment the pharmaceutical composition contains sucrose, L-histidine, L-histidine monohydrochloride monohydrate, EDTA disodium salt dihydrate, methionine and polysorbate 80. More preferably, the pharmaceutical composition comprises 5 mg/mL recombinant ustekinumab antibody, 1.8 mg/mL L-histidine/L-histidine monohydrochloride monohydrate, 0.4 mg/mL polysorbate 80, 85 mg/mL sucrose, 0.02 mg/ml EDTA disodium salt dihydrate, 0.4 mg/ml methionine and water for injection. Most preferably, the pharmaceutical composition consists of 5 mg/mL recombinant ustekinumab antibody, 1.8 mg/mL L-histidine/L-histidine monohydrochloride monohydrate, 0.4 mg/mL polysorbate 80, 85 mg/mL sucrose, 0.02 mg/ml EDTA disodium salt dihydrate, 0.4 mg/ml methionine and water for injection.

This pharmaceutical composition can be used in the treatment of adult patients with moderately to severely active Crohn's disease who have had an inadequate response with, lost response to, or were intolerant to either conventional therapy or a TNFα antagonist or have medical contraindications to such therapies.

The recommended dosage of ustekinumab for the treatment of adult patients with moderately to severely active Crohn's disease is 260 mg to 520 mg, depending on the body weight, administered by intravenous injection using the above pharmaceutical composition containing sucrose, L-histidine, L-histidine monohydrochloride monohydrate, EDTA disodium salt dihydrate, methionine and polysorbate 80. After this initial intravenous injection the following dose is administered by subcutaneous injection using the above pharmaceutical composition containing sucrose, L-histidine, L-histidine monohydrochloride monohydrate and polysorbate 80. The subcutaneous injections start eight weeks after the intravenous injection. The recommended doses of ustekinumab for subcutaneous administration are 90 mg every 8 weeks following the first s.c. injection.

The following examples are provided for illustrative purposes. It is thus understood that the examples are not to be construed as limiting. The skilled person in the art will clearly be able to envisage further modifications of the principles laid out herein.

EXAMPLES

The present invention is supported and illustrated by reference to the following non-limiting examples.

1. Production of the Ustekinumab Antibody in CHO Cells

CHO-K1 cells were transfected with a first expression vector expressing the heavy chain of ustekinumab under the control of a first promoter and additionally containing a first selection marker gene and a second expression vector expressing the light chain of ustekinumab under the control of said first promoter and additionally containing a second selection marker gene. Transfected cells were selected by treatment with substances matching to the selection marker genes and single clones of the CHO-K1 cells were obtained after some rounds of subculturing. The supernatant of these single clones was then purified by protein A chromatography and then subjected to glycoform characterisation and activity assays as described below.

2. Glycoform Characterisation 2.1 Sample Preparation

The protein sample was diluted with 5 mM Tris/HCl, pH 7.0 to a final concentration of 1.25 μg/μL. 1.5 μl PNGase F and 2.5 μL of 1.5% IGEPAL CA-630 were added to 120 μL of the diluted sample for the deglycosylation reaction. This mixture was incubated for 17 hours at 37° C., before the released N-glycans were purified from the protein by centrifugation with Amicon® Ultra-0.5 30K filter devices, wherein the filtrate contains the N-glycans. The filtrate was dried in a vacuum concentrator and then 10 μL derivatization solution (0.5 M 2-AB in DMSO/acetic solution) and 10 μL reduction solution (1 M sodium cyanoborohydride in DMSO/acetic solution) were added and the mixture was incubated for 17 hours at 37° C. The labelled N-glycans were purified from excess reagent by gel filtration using NAP-5 size exclusion columns. The flow-through of the column was collected, dried using a vacuum concentrator and the pellet was dissolved in 50% acetonitrile.

For identification of sialylated N-glycan peaks, the N-glycans were desialylated by mild acidic hydrolysis using 2 M acetic acid and incubation at 80° C. for two hours.

The resulting sample was subjected to HPLC using the following settings:

| | |
|---|---|
| Column: | XBridge Glycan BEH Amide XP Column 130 Å, 2.5 μm, 2.1 mm × 150 mm |
| Column temperature: | 60° C. |
| Auto sampler temperature: | 8° C. |
| Injection volume: | 2 μL |
| Detection: | FLD Ex 260 nm, Em 428 nm |
| Mobile phase A: | 100 mM ammonium formate in water, pH 5.0 |
| Mobile phase B: | Acetonitrile |

Gradient:

| Time [min] | Eluent B [% Acetonitrile] | Flow rate [mL/min] | Parameter |
|---|---|---|---|
| 0 | 72 | 0.34 | Separation |
| 70 | 50 | 0.34 | |
| 73 | 20 | 0.17 | Cleaning |
| 83 | 20 | 0.17 | |
| 85 | 72 | 0.17 | Equilibration |
| 95 | 72 | 0.17 | |
| 100 | 72 | 0.34 | |

The relative quantity of each N-glycan peak was calculated by comparing the area of a particular peak to the sum of all N-glycan peaks.

Table 1 shows the result of the glycoform analysis of three selected CHO subclones in comparison to three different batches of the reference product:

| Cell line | Description | ID | G0F [%] | G1F [%] | G2F [%] | Sialo + α-gal [%] |
|---|---|---|---|---|---|---|
| — | Reference product | 1 | 25.7 | 32.6 | 10.3 | 22.4 |

-continued

| Cell line | Description | ID | G0F [%] | G1F [%] | G2F [%] | Sialo + α-gal [%] |
|---|---|---|---|---|---|---|
| — | Reference product | 2 | 25.3 | 33.9 | 8.8 | 23.4 |
| — | Reference product | 3 | 26.6 | 35.3 | 9.1 | 23.6 |
| CHO-K1 | subclone | 485-11#8 | 66.6 | 24.2 | 2.5 | 0.2 |
| CHO-K1 | subclone | 567-7#54 | 58.4 | 28.2 | 3.9 | 0.9 |
| CHO-K1 | subclone | 563-24#103 | 53.2 | 34.2 | 5.4 | 1.1 |

It is apparent from the above results that the CHO-produced antibody molecules produced by the method of the present invention have a significantly lower content of sialic acids than the reference product. Further, they have a higher percentage of the G0F glycoform and a lower content of the G2F glycoform than the reference product.

For distinguishing between NANA and NGNA the N-glycans were labelled with the GlycoWorks RapiFluor-MS Kit of Waters. After elimination of excessive reagent and protein by HILIC solid-phase extraction, the N-glycans were separated via HILIC-UPLC equipped with a fluorescence detector (Waters, FLR) and a mass detector (Waters, Acquity QDa). For fluorescence signals with a relative peak area of >0.1%, QDa data were evaluated in the scan range from 350-1250 m/z. The peaks corresponding to glycoforms containing NANA and NGNA were identified by comparison to known N-glycan masses from the NIBRT glycobase 3.2 database.

Table 2 shows the results of a representative sialic acid analysis for clone 485-11 #8:

| | Reference product | CHO-produced ustekinumab |
|---|---|---|
| Total amount of glycoforms containing NANA | 0.5% | 0.3% |
| Total amount of glycoforms containing NGNA | 19.6% | not detectable |

This analysis shows that 100% of the sialic acid molecules present on the CHO-produced ustekinumab are NANA, whereas the reference product predominantly contains NGNA.

3. Determination of Charge Heterogeneity

The protein sample was diluted with 20 mM sodium phosphate buffer pH 7.5 to 1 mg/mL. Sample was injected onto the cation exchange column and separated according to their charge heterogeneity. Charge isoforms were eluted in a salt gradient and detected using an UV detector at 214 nm.

The following settings were used for determining charge heterogeneities by cation exchange (CEX) HPLC:

| | |
|---|---|
| Column: | Dionex, BioLCProPac ® WCX-10, 4.0 × 250 mm, 10 μm |
| Flow rate: | 1.0 mL/min |
| Column temperature: | 40° C. |
| Autosampler temperature: | 6° C. |
| Injection volume: | 25 μL (25 ug per injection) |
| UV Wavelength | 214 nm, 280 nm |
| Mobile phase A: | 20 mM sodium phosphate buffer pH 7.5 |
| Mobile phase B: | 25 mM NaCl; 20 mM sodium phosphate buffer pH 7.5 |

| Time [min] | Solvent composition [%-B] | Solvent composition [mM NaCl] |
|---|---|---|
| 0 | 15.0 | 3.75 |
| 10 | 15.0 | 3.75 |
| 60 | 100.0 | 25.0 |
| 62 | 100.0 | 25.0 |
| 63 | 15.0 | 3.75 |
| 70 | 15.0 | 3.75 |

Gradient:

Table 3 shows the area of the CEX main peak corresponding to antibody molecules without a C-terminal lysine residue (K0):

| | parental clone | subclone | area main K0 (%) |
|---|---|---|---|
| CHO | cl485-11 | 8 | 68.6 |
| | cl563-7 | 54 | 69.6 |
| | cl563-24 | 103 | 63.0 |
| reference product (mean of 12 samples) | —/— | —/— | 36.0 |

It is apparent from the above Table 3 that the ustekinumab produced by the method of the present invention has a considerably higher percentage of antibody molecules lacking both C-terminal lysines (referred to as K0) than the reference product.

4. Functional Characterisation of the Ustekinumab Antibody 4.1 IL23 ELISA

Nunc MaxiSorp® plates were coated with 50 μl of coating solution (0.5 μg/ml recombinant human IL-23 in PBS). After discarding the coating solution, the plates were washed three times with 350 μl washing buffer (0.1% polysorbate 20 in PBS) per well, before blocking the plates with 1% BSA in PBS and washing one time with the above washing buffer. After discarding the washing buffer, 50 μl of serially diluted antibody preparations were added to each well and the plates were incubated for two hours at room temperature. The plates were then washed three times with 350 μl washing buffer per well and 100 μl of horseradish peroxidase (HRP)-conjugated detection antibody (mouse anti-human IgG HRP conjugate) in 1% BSA/PBS were added to each well. The plates were incubated for 30 minutes at room temperature and then washed three times with 350 μl washing buffer per well. Then 100 μl of the HRP substrate 3,3',5,5'-tetramethylbenzidine (100 μg/ml in DMSO and citrate phosphate buffer, pH 5.0) was added and the plates were incubated. After 10 minutes it was started to measure the absorption at 650 nm and the reaction was stopped when the wells with the highest concentration of standard reached an absorbance value of 1 by adding 50 μl of 2 M sulphuric acid per well. Then the absorption was measured at 450 nm within 30 minutes. The calculation of the relative potency of the test samples was done with the PLA2.1 software.

Table 4 shows the results of the IL23 ELISA test:

| | parental clone | subclone | relative potency [U/mg] |
|---|---|---|---|
| CHO | cl485-11 | 8 | 1.02 |
| | cl563-7 | 54 | 1.02 |
| | cl563-24 | 103 | 0.95 |

-continued

| | parental clone | subclone | relative potency [U/mg] |
|---|---|---|---|
| reference product | —/— | —/— | 1.00 |

Table 4 shows that despite the differences in sialylation and the different distribution of the glycoforms the ustekinumab antibody produced in CHO cells shows essentially the same binding to its target IL-23 as the reference product.

4.2 IL-12 Binding

The binding affinity of ustekinumab biosimilar to IL-12 was analyzed using Biolayer Interferometry (BLI) with an Octet RED96 system (ForteBio). Ustekinumab was immobilized at 0.5 μg/mL using anti-Human IgG Fc Capture (AHC) biosensors and recombinant human IL-12 was allowed to bind in 3 concentrations (0.2, 0.1 and 0.05 μg/mL) for 600 seconds and to dissociate for 2400 seconds. Measurements were done in PBS containing 0.1% BSA and 0.02% Tween20, pH 7.2 at 30° C. The data were evaluated with the Data Analysis 9.0 Software using a 1:1 binding model.

Table 5 shows the results of the IL-12 binding test:

| | | | BLI-IL-12 | | |
|---|---|---|---|---|---|
| | parental clone | subclone | $K_D$ [M] | $k_{on}$ | $k_{off}$ |
| CHO | cl563-7 | 54 | 2.08E−10 | 4.75E+05 | 9.73E−05 |
| | cl563-24 | 103 | 1.90E−10 | 5.14E+05 | 9.72E−05 |
| reference product | —/— | —/— | 2.06E−10 | 4.43E+05 | 8.94E−05 |

Similar to the results for IL-23 binding, Table 5 shows that despite the differences in sialylation and the different distribution of the glycoforms the ustekinumab antibody produced in CHO cells shows essentially the same binding to its target IL-12 as the reference product.

4.3 FcRn Binding

The binding of the ustekinumab biosimilar to FcRn was measured using bio-layer interferometry (BLI). Both the FcRn ligand and the antibody samples were diluted in a 96-well plate according to a predetermined scheme using kinetic buffer (0.01% BSA, 0.02% polysorbate 20 in DPBS). Binding of ustekinumab to FcRn was analyzed at pH 6.0 and 30° C. in kinetic buffer using an Octet RED96 System (Pall-ForteBio). The data were evaluated with the Data Analysis 9.0 Software using a 1:1 binding model.

Table 6 shows the results of the FcRn binding test:

| | | | BLI-FcRn | | |
|---|---|---|---|---|---|
| | parental clone | subclone | KD [M] | kon | koff |
| CHO | cl485-11 | 8 | 8.96E−10 | 8.78E+05 | 7.79E−04 |
| | cl563-7 | 54 | 9.16E−10 | 8.50E+05 | 7.78E−04 |
| | cl563-24 | 103 | 9.18E−10 | 8.78E+05 | 8.08E−04 |
| reference product | —/— | —/— | 8.84E−10 | 8.39E+05 | 7.40E−04 |

It is apparent from Table 6 that the ustekinumab antibody produced in CHO cells shows essentially the same binding to FcRn as the reference product.

4.3 IFNγ Release

The relative biological activity of the reference product and the ustekinumab biosimilar was measured by its inhibition of IL-12 induced IFN-γ production in a human natural killer lymphoma cell line (NK-92).

Stimulation of NK-92 cells with IL-12 induces expression of IFN-γ which is secreted from the cells into the medium supernatant. Ustekinumab which binds and neutralizes the p40 subunit of IL-12 inhibits binding of IL-12 to its cell surface receptors IL12RB1 and IL12RB2, which subsequently results in inhibition of IFN γ-expression. The IFN-γ concentration in the medium is detected with a sandwich enzyme linked immunosorbance assay (ELISA).

The relative potency is determined by comparison of the inhibitory effect of the test sample to a reference substance.

NK-92 cells were cultured in suspension at 37° C. in α-MEM containing 12.5% FCS, 12.5% horse serum and 1% glutamine. IL-2 was added to the medium in a final concentration of 20 ng/ml. Before the assay for IFNγ secretion was started, the cells were IL-2-starved overnight. Serial dilutions of the reference substance and the test samples were prepared. Before treatment of the NK-92 cells the antibody samples were pre-incubated with IL-12 for one hour to allow binding of the antibody to IL-12. $5\times10^4$ NK-92 cells per ml culture medium were seeded in one well of a 96-well plate in IL2-containing medium and then treated with 100 μl of the pre-incubated samples. The cells were incubated for 24 hours at 37° C. and then the supernatants were harvested.

To determine the IFN-gamma concentration in the supernatants, the Duo Set IFN-gamma ELISA Kit in combination with the Duo Set Ancillary Reagent Kit 2 of R&D Systems were used according to the manufacturer's instructions. The relative potency (RP) was calculated using the PLA2.1 software.

Table 7 shows the results of the IFNγ release test:

| | parental clone | subclone | NK-Assay RP [U/mg] |
|---|---|---|---|
| CHO | cl485-11 | 8 | 1.10 |
| | cl563-7 | 54 | 1.09 |
| | cl563-24 | 103 | 0.98 |

-continued

| | parental clone | subclone | NK-Assay RP [U/mg] |
|---|---|---|---|
| reference product | —/— | —/— | 1.00 |

It is apparent from Table 7 that the ustekinumab antibody produced in CHO cells inhibits IFNγ release from NK-92 cells to substantially the same degree as the reference product.

5. Additional Analysis of Clone Number c1563-24, Subclone 103

Clone number c1563-24, subclone 103, transfected as described in FIG. 1 was cultured in commercially available media in the fed batch mode. After 15 days of culture the cell supernatant was removed and purified by protein A chromatography. The resulting antibody preparation was subjected to glycoform characterisation using HILIC-UPLC as described in example 2 for the distinction between NANA and NGNA. The results of this analysis are shown in Table 8 below.

TABLE 8

| N-Glycan structure | Relative quantity in biosimilar product (%) | Relative quantity in reference product (%) |
|---|---|---|
| Total afucosylation | 3.2 | 6.0 |
| Total high mannose | 0.8 | 0.9 |
| Total sialylation | 1.3 | 20.3* |
| Total galactosylation | 36.4 | 47.3 |

*includes α-Gal

Additionally, the results of the activity assays are shown in Tables 9 to 11 below:

TABLE 9

| FeRn binding - d15 | |
|---|---|
| $K_D$ | 9.01E−10 |
| $K_{on}$ | 8.63E+05 |
| $K_{off}$ | 7.78E−04 |

TABLE 10

| Relative potency (Cell-based NK92) d15 | |
|---|---|
| Relative potency | 1.078 |

TABLE 11

| Relative potency (IL23-ELISA) d15 | |
|---|---|
| Relative potency | 1.053 |

Some Embodiments of the Present Invention Relate to

1. Composition containing an ustekinumab antibody, wherein the antibody has a sialic acid content of 0 to 5%.
2. Composition according to item 1, wherein more than 90% of the sialic acid is N-acetylneuraminic acid.
3. Composition according to item 1 or 2, wherein less than 10% of the sialic acid is N-glycolylneuraminic acid.
4. Composition according to any one of the preceding items, wherein at least 50% of the ustekinumab molecules within the composition do not comprise a C-terminal lysine.
5. Method for producing the composition according to any one of the preceding items, comprising culturing CHO cells which are genetically modified to express the ustekinumab antibody in a suitable culture medium.
6. Method according to item 5, wherein the CHO cells are CHO-K1 cells or cells derived therefrom.
7. Method according to item 5 or 6, wherein the CHO cells are cultured in fed-batch mode.
8. Method according to any one of items 5 to 7, further comprising a step of purifying the ustekinumab antibody.
9. Composition according to any one of items 1 to 4, being a pharmaceutical composition.
10. Pharmaceutical composition according to item 9, further containing sucrose, L-histidine, L-histidine monohydrochloride monohydrate and polysorbate 80.
11. Pharmaceutical composition according to item 9 or 10, containing 90 mg/mL ustekinumab, 1 mg/mL L-histidine/L-histidine monohydrochloride monohydrate, 0.04 mg/mL polysorbate 80 and 76 mg/mL sucrose in water for injection.
12. Pharmaceutical composition according to any one of items 9 to 11 for use in treating plaque psoriasis or psoriatic arthritis.

The invention claimed is:

1. A method of producing a recombinant ustekinumab antibody comprising the heavy chain and the light chain of ustekinumab, wherein the heavy chain and the light chain together form the recombinant ustekinumab antibody, the method comprising, a) culturing Chinese Hamster Ovary (CHO) host cells, genetically modified to express the heavy chain and the light chain of ustekinumab, in a suitable culture medium under conditions that allow the cells to express the heavy chain and the light chain and to form the recombinant ustekinumab antibody, b) harvesting the recombinant ustekinumab antibody from the host cell culture to obtain a recombinant ustekinumab antibody preparation, and c) purifying the recombinant ustekinumab antibody preparation obtained from harvesting by one or more purification step(s), wherein the recombinant ustekinumab antibody is a biosimilar of the ustekinumab reference product, wherein the ustekinumab reference product is produced in murine myeloma cells.

2. The method of claim 1, wherein the heavy chain of the recombinant ustekinumab has the sequence according to SEQ ID No. 1 and the light chain of the ustekinumab has the sequence according to SEQ ID No. 2.

3. The method of claim 1, wherein the ustekinumab reference product comprises a heavy chain according to SEQ ID No. 1 and a light chain according to SEQ ID No. 2.

4. The method of claim 1, wherein the CHO host cells are CHO-Kl cells or cells derived therefrom.

5. The method of claim 1, wherein the recombinant ustekinumab antibody is produced in large scale.

6. The method of claim 1, comprising combining the recombinant ustekinumab antibody from the recombinant ustekinumab antibody preparation one or more pharmaceutically acceptable excipient(s) to obtain a recombinant ustekinumab antibody drug product.

7. The method of claim 6, wherein the one or more pharmaceutically acceptable excipient(s) is/are selected from the group consisting of sucrose, L-histidine, L-histidine monohydrochloride monohydrate and polysorbate 80.

8. The method of claim 6, wherein the one or more pharmaceutically acceptable excipient(s) is/are selected from the group consisting of sucrose, L-histidine, L-histidine monohydrochloride monohydrate, methionine, EDTA disodium salt dihydrate and polysorbate 80.

9. The method of claim 7, wherein the recombinant ustekinumab antibody drug product comprises 90 mg/mL recombinant ustekinumab antibody and one or more pharmaceutically acceptable excipient(s) selected from the group consisting of 76 mg/mL sucrose, 1 mg/mL L-histidine/L-histidine monohydrochloride monohydrate and 0.04 mg/mL polysorbate 80.

10. The method of claim 8, wherein the recombinant ustekinumab antibody drug product comprises 5 mg/mL recombinant ustekinumab antibody and one or more pharmaceutically acceptable excipient(s) selected from the group consisting of 85 mg/mL sucrose, 1.8 mg/mL L-histidine/L-histidine monohydrochloride monohydrate, 0.4 mg/mL methionine, 0.02 mg/mL EDTA disodium salt dihydrate and 0.4 mg/mL polysorbate 80.

11. The method of claim 1, comprising determining that the recombinant ustekinumab antibody in the recombinant ustekinumab antibody preparation obtained in step b) or c) meets one or more of the following criteria (i) to (ii):

(i) binding to IL-23 differs from that of the ustekinumab reference product by not more than 20% or, (ii) binding to IL-12 differs from that of the ustekinumab reference product by not more than 20%.

12. The method of claim 1, comprising determining that the recombinant ustekinumab antibody in the recombinant ustekinumab antibody preparation obtained in step b) or c) meets one or more of the following criteria (iii) to (vi):

(iii) lower percentage of recombinant ustekinumab antibody molecules comprise c-terminal lysine, (iv) higher percentage of sialic acid being N-acetylneuraminic acid, (v) lower percentage of sialic acid being N-glycolylneuraminic acid or, (vi) lower content of afucosylated glycoforms, as compared to the ustekinumab reference product.

13. The method of claim 1, comprising determining that the recombinant ustekinumab antibody in the recombinant ustekinumab antibody preparation obtained in step b) or c) meets one or more of the following criteria (vii) to (x):

(vii) greater than 90% of the sialic acid being N-acetylneuraminic acid, (viii) less than 10% of the sialic acid being N-glycolylneuraminic acid, (ix) content of afucosylated glycoforms is less than 8% or, (x) content of terminal a-galactose is less than or equal to 0.1%.

14. The method of claim 11, wherein the binding to IL-23, and/or IL-12 is determined by Enzyme linked immunosorbent assay (ELISA) or bio-layer interferometry.

15. The method of claim 12, wherein the recombinant ustekinumab antibody molecules comprising c-terminal lysine are measured by cation exchange chromatography (CEX).

16. The method of claim 12, wherein the N-acetylneuraminic acid and N-glycolylneuraminic acid are measured by hydrophilic interaction liquid chromatography-ultra performance liquid chromatography HILIC-UPLC.

17. The method of claim 13, wherein the N-acetylneuraminic acid, N-glycolylneuraminic acid afucosylated glycoforms, and a-galactose are measured by hydrophilic interaction liquid chromatography-ultra performance liquid chromatography HILIC-UPLC.

18. A biosimilar recombinant ustekinumab antibody produced by the method of claim 1.

19. The biosimilar recombinant ustekinumab of claim 18, wherein the biosimilar recombinant ustekinumab antibody meets one or more of the following criteria:
(i) binding to IL-23 differs from that of the ustekinumab reference product by not more than 20% or,
(ii) binding to IL-12 differs from that of the ustekinumab reference product by not more than 20%.

20. The biosimilar recombinant ustekinumab antibody of claim 18, wherein the biosimilar recombinant ustekinumab antibody meets one or more of the following criteria:
(iii) lower percentage of recombinant ustekinumab antibody molecules comprise c-terminal lysine,
(iv) higher percentage of sialic acid being N-acetylneuraminic acid,
(v) lower percentage of sialic acid being N-glycolylneuraminic acid,
(vi) lower content of afucosylated glycoforms,
as compared to the ustekinumab reference product.

21. The biosimilar recombinant ustekinumab antibody of claim 18, wherein the biosimilar recombinant ustekinumab antibody meets one or more of the following criteria:
(vii) greater than 90% of the sialic acid being N-acetylneuraminic acid,
(viii) less than 10% of the sialic acid being N-glycolylneuraminic acid,
(ix) content of afucosylated glycoforms is less than 8% or,
(x) content of terminal a-galactose is less than or equal to 0.1%.

22. A biosimilar recombinant ustekinumab antibody produced in CHO cells, wherein the recombinant ustekinumab antibody is a biosimilar of a ustekinumab reference product, wherein the ustekinumab reference product is produced in murine myeloma cells.

23. The biosimilar recombinant ustekinumab antibody of claim 22, comprising a heavy chain and a light chain, wherein the heavy chain has the sequence according to SEQ ID No. 1 and the light chain has the sequence according to SEQ ID No. 2, wherein the recombinant ustekinumab antibody is a biosimilar of the ustekinumab reference product, wherein the ustekinumab reference product is produced in murine myeloma cells.

24. The biosimilar recombinant ustekinumab antibody of claim 22, comprising a heavy chain and a light chain, wherein the heavy chain has the sequence according to SEQ ID No. 1 and the light chain has the sequence according to SEQ ID No. 2, wherein the recombinant ustekinumab antibody is a biosimilar of the ustekinumab reference product, wherein the ustekinumab reference product is produced in murine myeloma cells, and wherein the ustekinumab reference product comprises a heavy chain according to SEQ ID No. 1 and a light chain according to SEQ ID No. 2.

25. The biosimilar recombinant ustekinumab antibody of claim 22 that meets one or more of the following criteria:
(i) binding to IL-23 differs from that of the ustekinumab reference product by not more than 20%,
(ii) binding to IL-12 differs from that of the ustekinumab reference product by not more than 20%,
(iii) lower percentage of recombinant ustekinumab antibody molecules comprise c-terminal lysine as compared to the ustekinumab reference product,
(iv) higher percentage of sialic acid being N-acetylneuraminic acid as compared to the ustekinumab reference product,
(v) lower percentage of sialic acid being N-glycolylneuraminic acid as compared to the ustekinumab reference product,
(vi) lower content of afucosylated glycoforms as compared to the ustekinumab reference product,
(vii) greater than 90% of the sialic acid being N-acetylneuraminic acid,
(viii) less than 10% of the sialic acid being N-glycolylneuraminic acid,
(ix) content of afucosylated glycoforms is less than 8% or,
(x) content of terminal a-galactose is less than or equal to 0.1%,
wherein the ustekinumab reference product is produced in murine myeloma cells.

26. The biosimilar recombinant ustekinumab antibody of claim 22, having a heavy chain according to SEQ ID No. 1 and a light chain according to SEQ ID NO: 2 that meets one or more of the following criteria:
(i) binding to IL-23 differs from that of the ustekinumab reference product by not more than 20%,
(ii) binding to IL-12 differs from that of the ustekinumab reference product by not more than 20%,
(iii) lower percentage of recombinant ustekinumab antibody molecules comprise c-terminal lysine as compared to the ustekinumab reference product,
(iv) higher percentage of sialic acid being N-acetylneuraminic acid as compared to the ustekinumab reference product,
(v) lower percentage of sialic acid being N-glycolylneuraminic acid as compared to the ustekinumab reference product,
(vi) lower content of afucosylated glycoforms as compared to the ustekinumab reference product,
(vii) greater than 90% of the sialic acid being N-acetylneuraminic acid,
(viii) less than 10% of the sialic acid being N-glycolylneuraminic acid,
(ix) content of afucosylated glycoforms is less than 8% or,
(x) content of terminal a-galactose is less than or equal to 0.1%,
wherein the ustekinumab reference product is produced in murine myeloma cells, and wherein the ustekinumab reference product comprises a heavy chain according to SEQ ID No. 1 and a light chain according to SEQ ID No. 2.

* * * * *